(12) United States Patent
Itoi

(10) Patent No.: US 9,000,164 B2
(45) Date of Patent: Apr. 7, 2015

(54) ORGANIC ELECTROLUMINESCENCE MATERIAL INCLUDING A SUBSTITUTED PHENAZINE GROUP AND ORGANIC ELECTROLUMINESCENCE DEVICE INCLUDING THE SAME

(71) Applicant: Samsung Display Co., Ltd., Yongin, Gyeonggi-Do (KR)

(72) Inventor: Hiroaki Itoi, Yongin (KR)

(73) Assignee: Samsung Display Co., Ltd., Yongin, Gyeonggi-Do (KR)

( * ) Notice: Subject to any disclaimer, the term of this patent is extended or adjusted under 35 U.S.C. 154(b) by 0 days.

(21) Appl. No.: 14/057,151

(22) Filed: Oct. 18, 2013

(65) Prior Publication Data

US 2014/0114063 A1   Apr. 24, 2014

(30) Foreign Application Priority Data

Oct. 18, 2012   (JP) ................. 2012-230969

(51) Int. Cl.
| | |
|---|---|
| *C07D 241/48* | (2006.01) |
| *H01L 51/00* | (2006.01) |
| *C07D 401/04* | (2006.01) |
| *C07D 241/46* | (2006.01) |
| *H01L 51/50* | (2006.01) |

(52) U.S. Cl.
CPC ........ *H01L 51/0072* (2013.01); *H01L 51/0067* (2013.01); *C07D 401/04* (2013.01); *C07D 241/46* (2013.01); *H01L 51/5056* (2013.01); *H01L 51/5088* (2013.01); *H01L 51/0059* (2013.01)

(58) Field of Classification Search
CPC .................................................. C07D 241/48
USPC ........................................................ 544/347
See application file for complete search history.

(56) References Cited

FOREIGN PATENT DOCUMENTS

| | | |
|---|---|---|
| JP | 2004-146110 A | 5/2004 |
| JP | 2004-281408 A | 10/2004 |
| WO | WO 2012/011756 A1 | 1/2012 |

OTHER PUBLICATIONS

Okamoto, et al.; "Facile Synthesis of 5, 10-Diaryl-5, 10-dihydrophenazines and Application to EL Devices," Organic Letters, 2003, pp. 373-376, vol. 5, No. 3; American Chemical Society; USA.

Terada, et al.; "Exchange Interaction of 5,5'-(m-and-p-Phenylene)bis(10-phenyl-5,10-dihydrophenazine) Dictations and Related Analogues," J. Org. Chem.; 2005; pp. 10073-10081; 70, American Chemical Society; USA.

*Primary Examiner* — Douglas M Willis

(74) *Attorney, Agent, or Firm* — Lee & Morse, P.C.

(57) ABSTRACT

An organic electroluminescence (EL) material and an organic EL device including the same, the organic electroluminescence (EL) material being represented by following Chemical Formula 1:

9 Claims, 1 Drawing Sheet

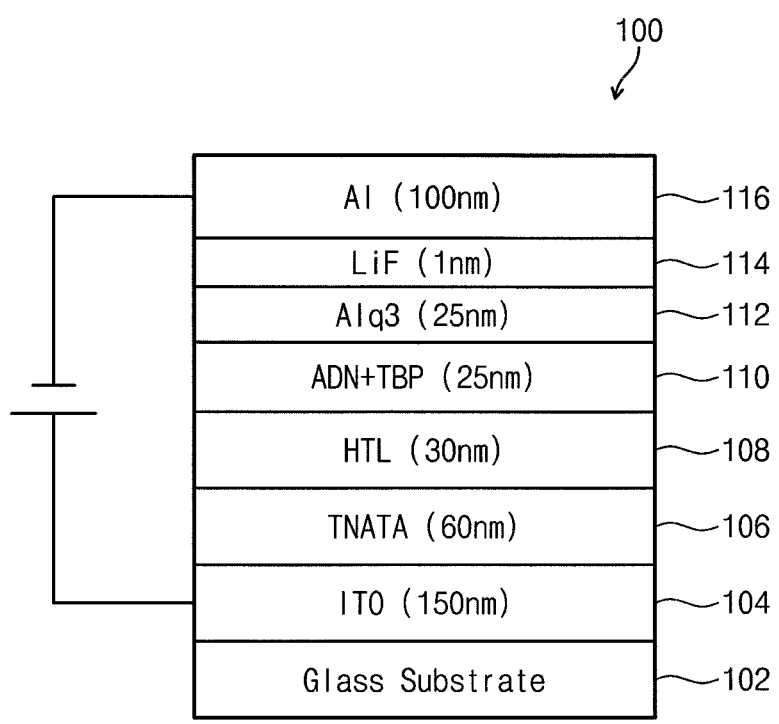

ORGANIC ELECTROLUMINESCENCE MATERIAL INCLUDING A SUBSTITUTED PHENAZINE GROUP AND ORGANIC ELECTROLUMINESCENCE DEVICE INCLUDING THE SAME

CROSS-REFERENCE TO RELATED APPLICATION

Japanese Patent Application No. 2012-230969, filed on Oct. 18, 2012, in the Japanese Patent Office, and entitled: "ORGANIC ELECTROLUMINESCENCE MATERIAL INCLUDING AMINE DERIVATIVE INCLUDING 5,10-DIARYL-5,10-DIHYDROPHENAZINE AND ORGANIC ELECTROLUMINESCENCE DEVICE USING THE SAME," is incorporated by reference herein in its entirety.

BACKGROUND

1. Field

Embodiments relate to an organic electroluminescence (EL) material and an organic EL device including the same.

2. Description of the Related Art

Recently, development on an organic EL display apparatus as an image display apparatus has been considered. Different from a liquid crystal display apparatus, the organic EL display apparatus is a self-emission type display apparatus in which an image is displayed through recombining holes and electrons (injected from an anode and a cathode, respectively) in an emission layer, and through emitting light from an emitting material including an, e.g., organic, compound in the emission layer.

An EL device may include, e.g., an organic EL device including an anode, a hole transport layer on the anode, an emission layer on the hole transport layer, an electron transport layer on the emission layer, and a cathode on the electron transport layer. The holes may be injected from the anode, and the injected holes may be injected layer. The holes may be injected from the anode, and the injected holes may be injected via the hole transport layer into the emission layer. The electrons may be injected from the cathode, and the injected electrons may be injected via the electron transport layer to the emission layer. Through the recombination of the holes and the electrons injected into the emission layer, excitons are produced in the emission layer. The organic EL device may emit light using the light generated from the radiation and deactivation of the excitons. The organic EL device may include various modifications and is not limited to the constitution explained above.

SUMMARY

Embodiments are directed to an organic electroluminescence (EL) material and an organic EL device including the same.

The embodiments may be realized by providing an organic electroluminescence (EL) material represented by following Chemical Formula 1:

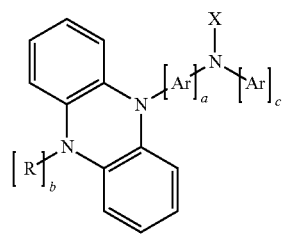

(1)

wherein X is a monovalent group represented by one of following Chemical Formulae (2) to (14), each Ar is independently an aryl group having 6 to 18 carbon atoms or a heteroaryl group having 6 to 18 carbon atoms, R is an aryl group having 6 to 18 carbon atoms, a heteroaryl group having 6 to 18 carbon atoms, or an alkyl group having 1 to 12 carbon atoms, and a to c are natural numbers satisfying a<3, b<3, and c<3, and a, b, and c do not equal zero,

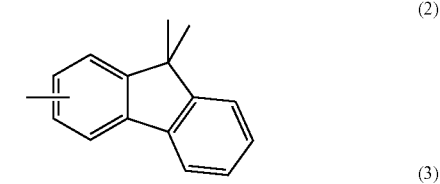

(2)

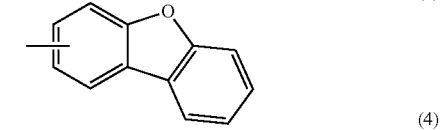

(3)

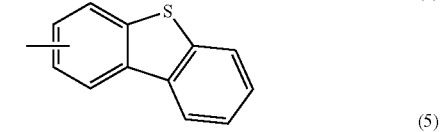

(4)

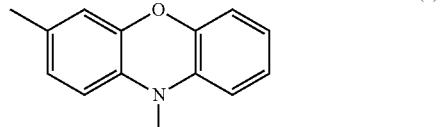

(5)

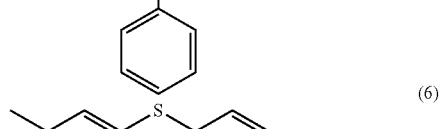

(6)

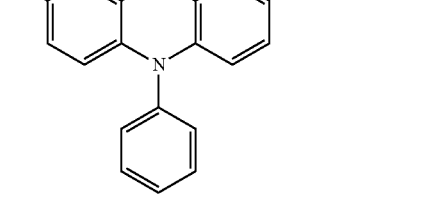

(7)

-continued
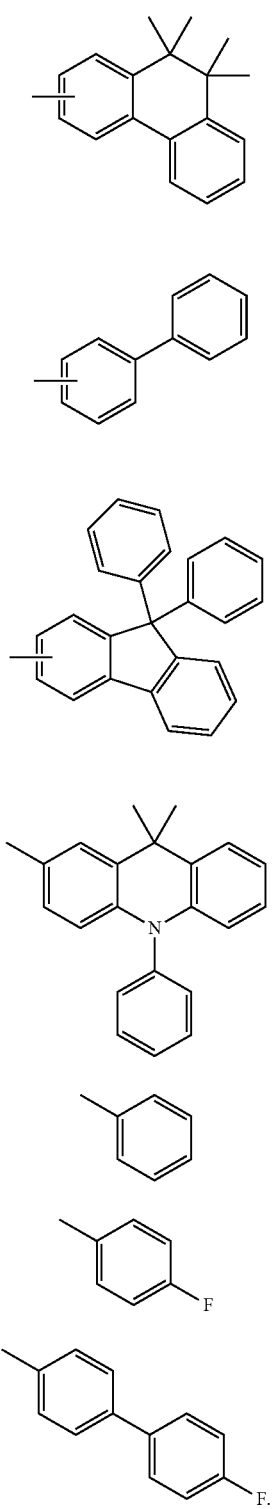
(8)
(9)
(10)
(11)
(12)
(13)
(14)
The organic EL material represented by Chemical Formula (1) may be a hole transporting material.
The organic EL material represented by Chemical Formula (1) may be a hole injecting material.
The organic EL material represented by Chemical Formula (1) may be one of Compounds 1 to 13, below:
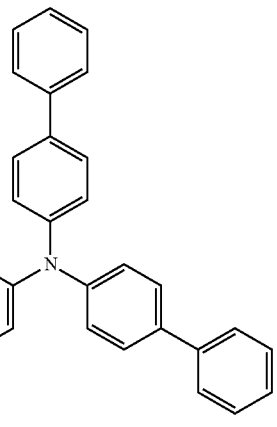
1
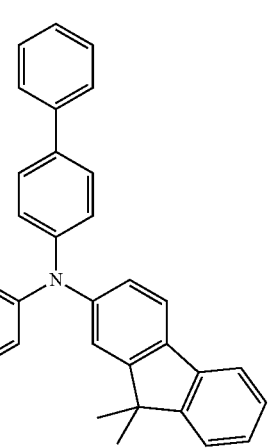
2
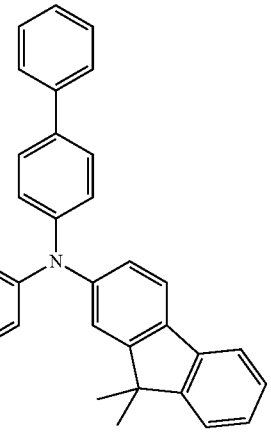
3

-continued
4
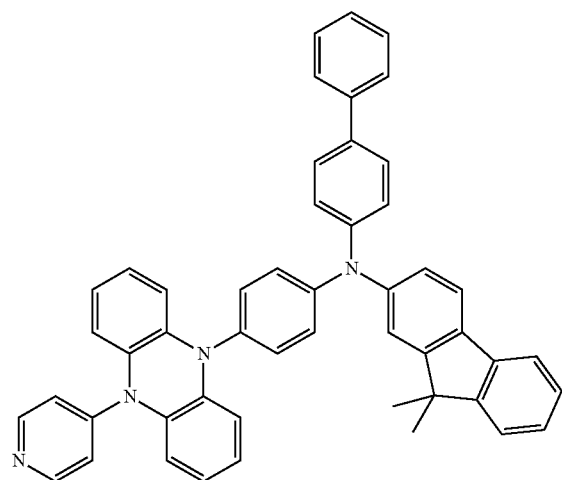
5
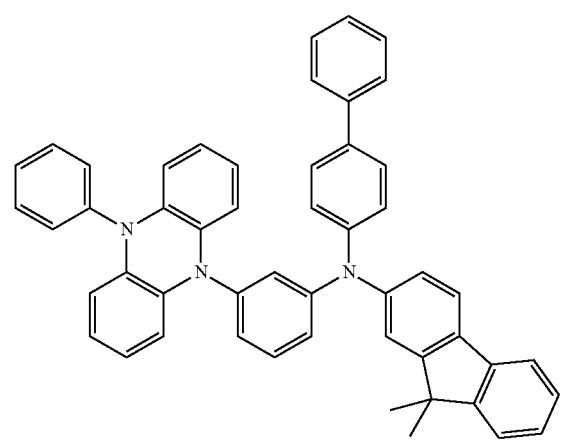
6
-continued
7
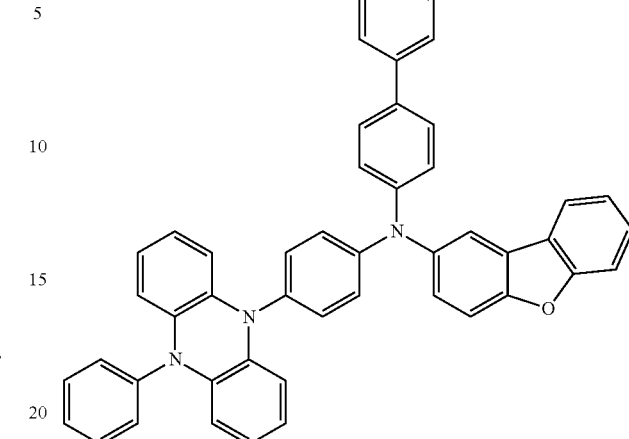
8
9
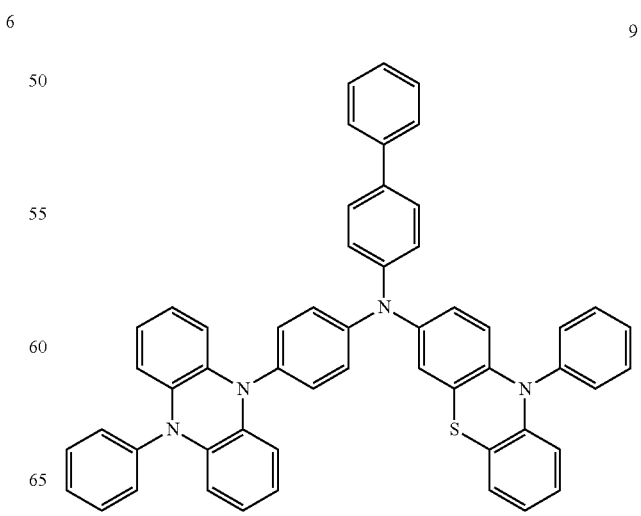

-continued

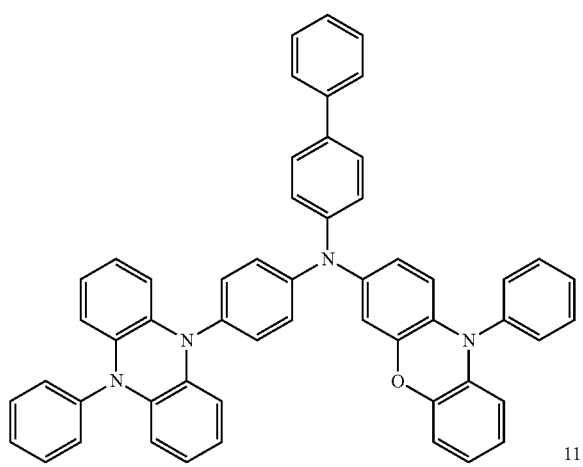

10

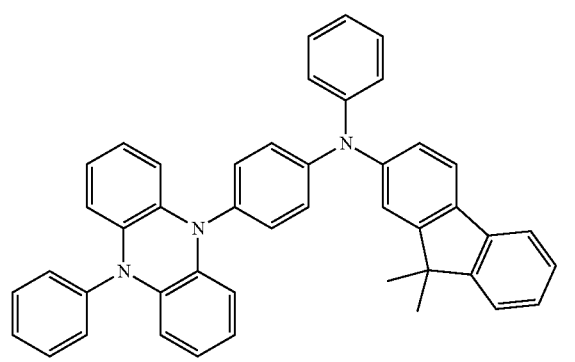

11

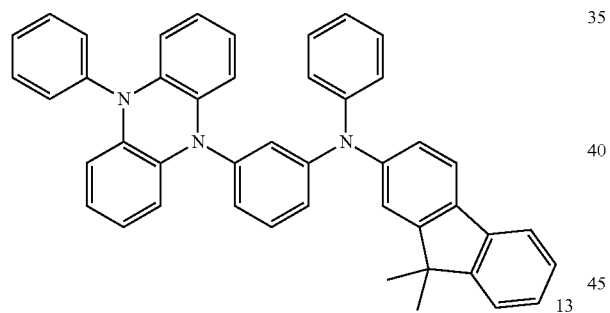

12

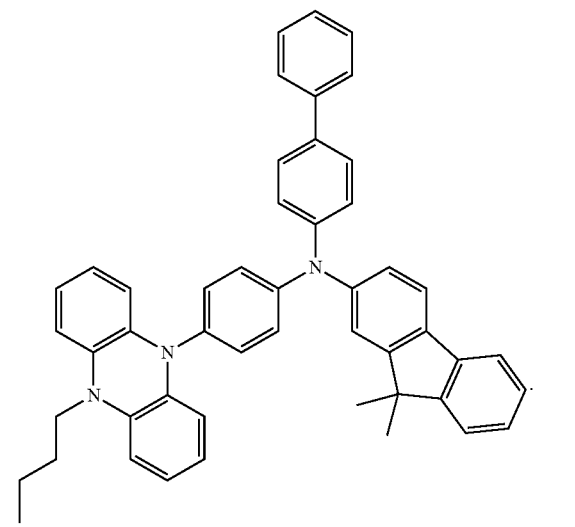

13

The embodiments may also be realized by providing an organic EL device comprising an organic EL material represented by following Chemical Formula (1):

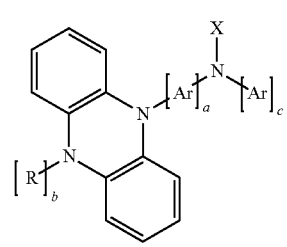

(1)

wherein X is a monovalent group represented by one of following Chemical Formulae (2) to (14), each Ar is independently an aryl group having 6 to 18 carbon atoms or a heteroaryl group having 6 to 18 carbon atoms, R is an aryl group having 6 to 18 carbon atoms, a heteroaryl group having 6 to 18 carbon atoms, or an alkyl group having 1 to 12 carbon atoms, and a to c are natural numbers satisfying a<3, b<3, and c<3, and a, b, c do not equal zero,

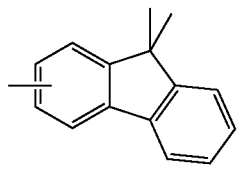

(2)

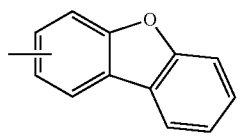

(3)

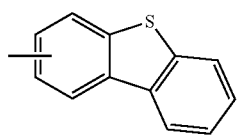

(4)

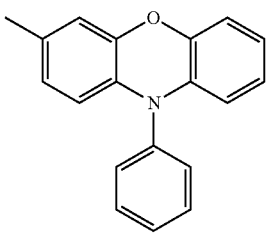

(5)

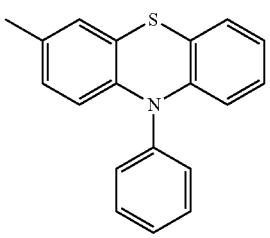

(6)

-continued
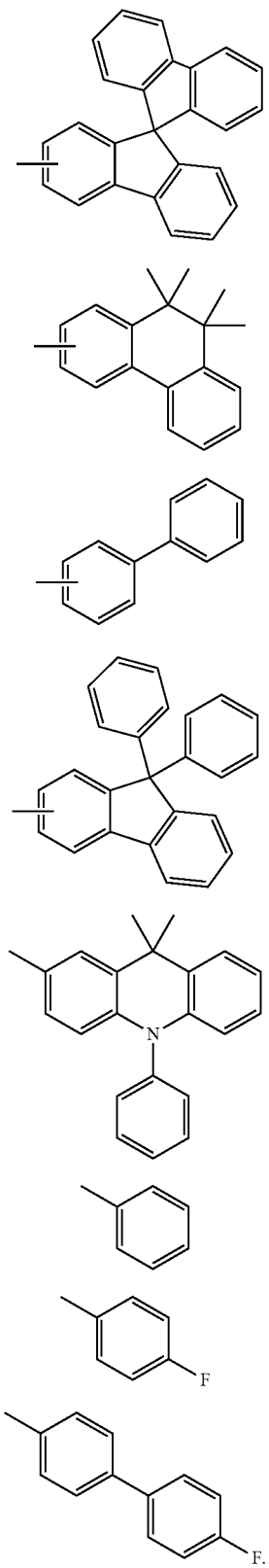
The organic EL material may be a hole transporting material.
The organic EL material may be a hole injecting material.
The organic EL material represented by Chemical Formula (1) may be one of Compounds 1 to 13, below:
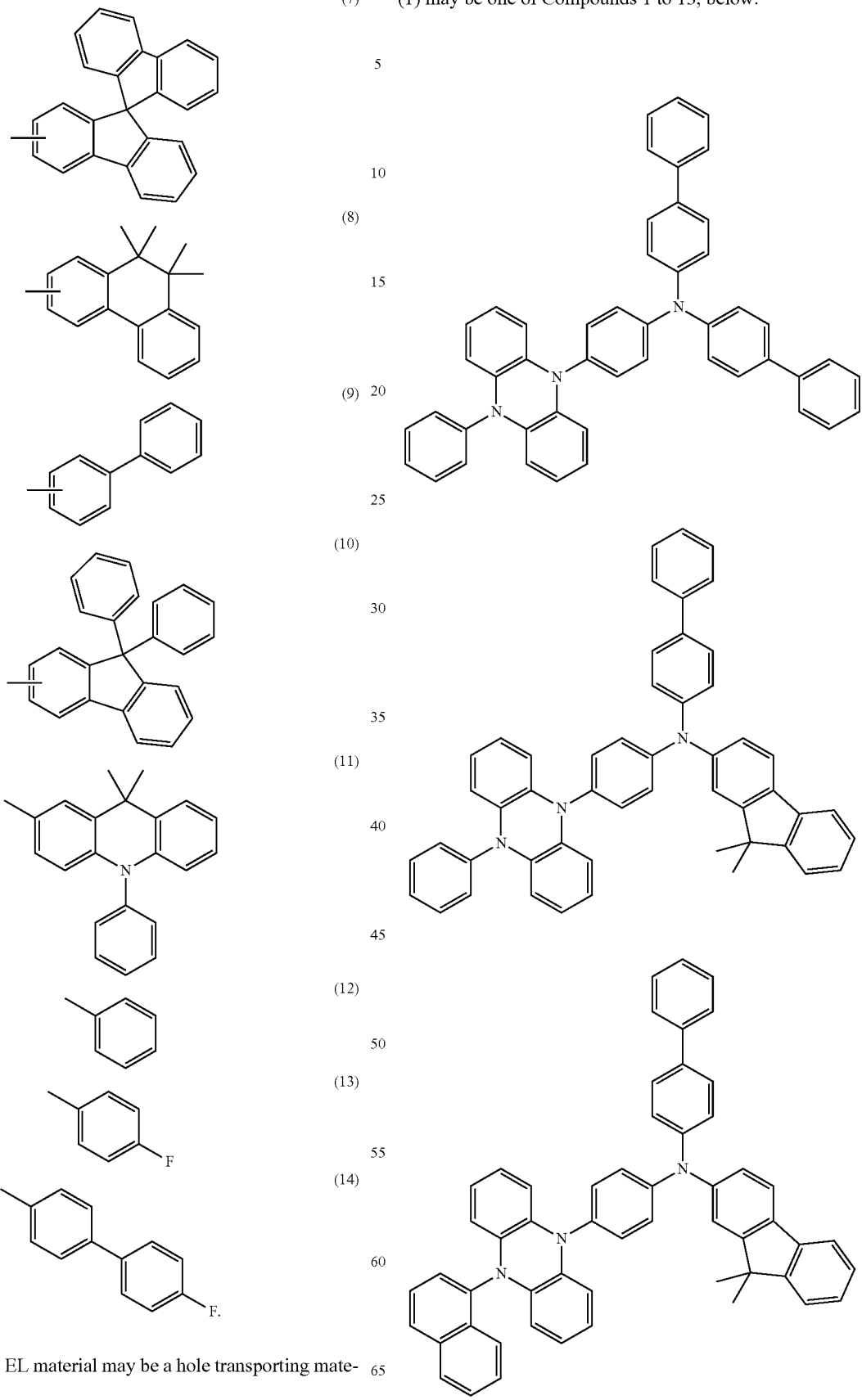

11
-continued
4
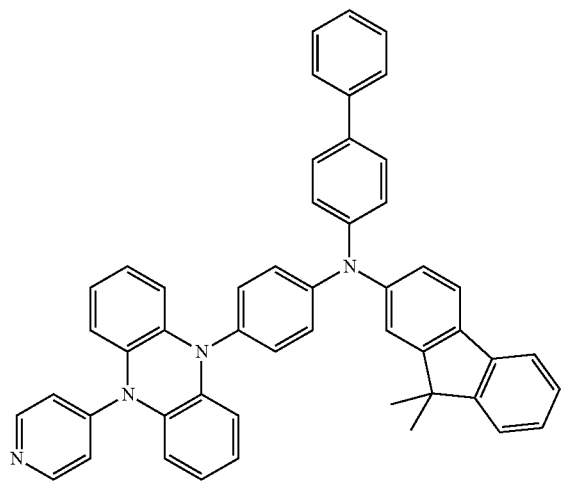
5
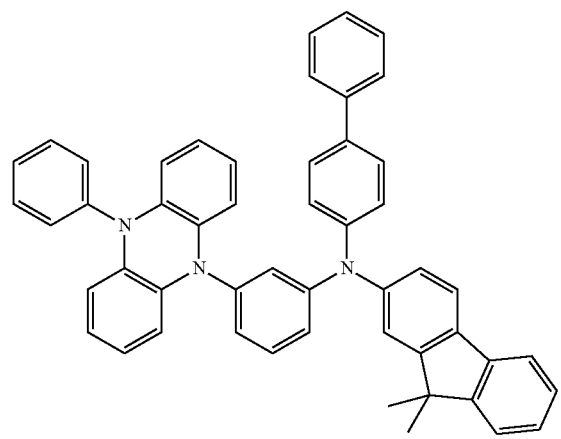
6
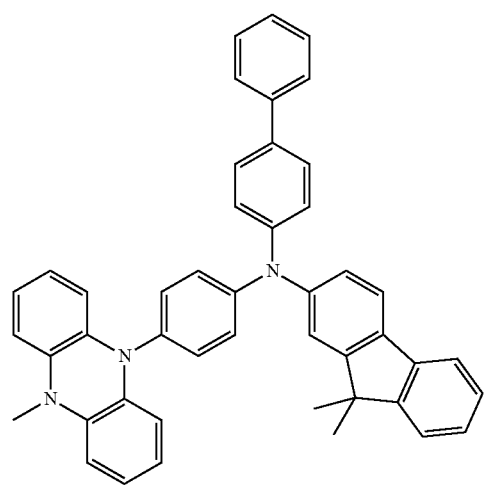
12
-continued
7
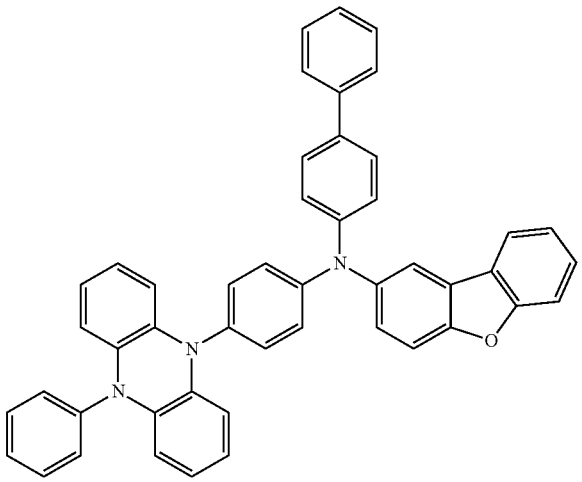
8
9

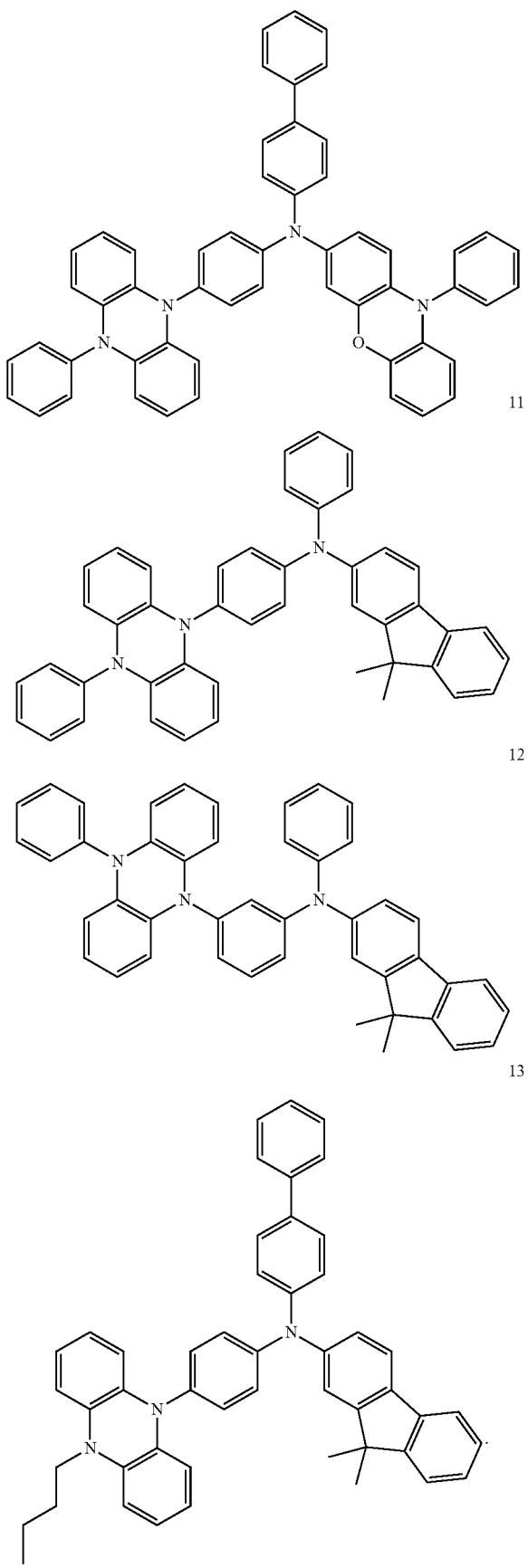

BRIEF DESCRIPTION OF THE DRAWING

Features will be apparent to those of skill in the art by describing in detail exemplary embodiments with reference to the attached drawing in which:

FIG. 1 is a schematic diagram of elements of an organic EL device according to an embodiment.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. Like reference numerals refer to like elements throughout.

Embodiments provide a compound or material for an electroluminescence device. In an implementation, the compound may include an amine derivative, e.g., a 5,10-diaryl-5,10-dihydrophenazine group. In an implementation, the compound or material according to an embodiment may be used as a hole transporting material applicable in a hole transport layer of an organic EL device. An organic EL device including the material according to an embodiment may exhibit improved emission efficiency and increased lifetime.

The embodiments may provide a compound for an electroluminescence device. In an implementation, the compound may be an amine derivative. The amine derivative according to an embodiment may include, e.g., a 5,10-diaryl-5,10-dihydrophenazine group. The compound according to an embodiment may be used as the hole transporting material of the hole transport layer of an organic EL device. In an implementation, the compound according to an embodiment may be represented by the following Chemical Formula (1).

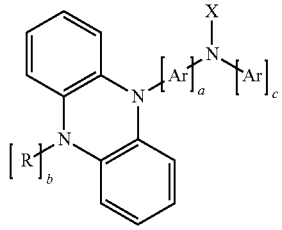

(1)

In Chemical Formula (1), X may be a monovalent group represented by one of following Chemical Formulae (2) to (14). In an implementation, * represents a bonding site with a nitrogen atom of Chemical Formula (1).

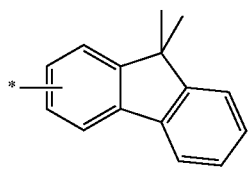

(2)

-continued (3) 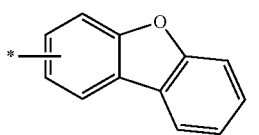

(4) 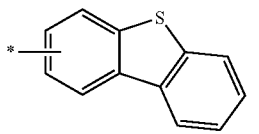

(5) 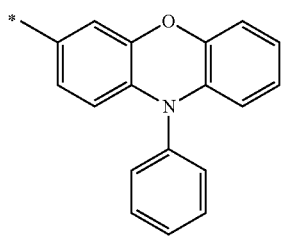

(6) 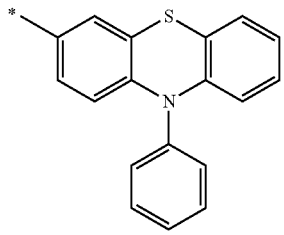

(7) 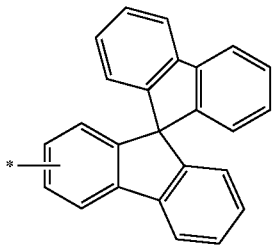

(8) 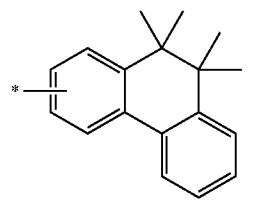

(9) 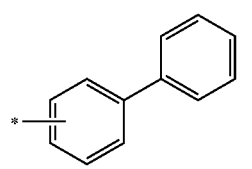

-continued

(10) 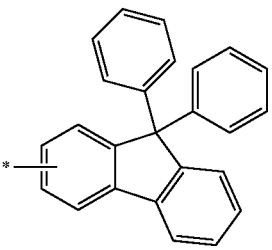

(11) 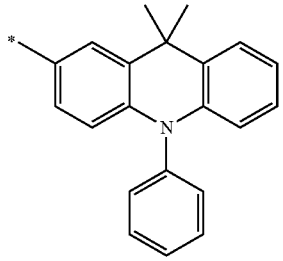

(12) 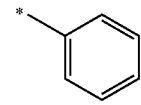

(13) 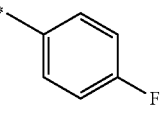

(14) 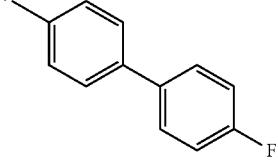

In Chemical Formula (1), each Ar may independently be an aryl group having 6 to 18 carbon atoms or a heteroaryl group having 6 to 18 carbon atoms. For example, the Ar bracketed by 'a' may be an arylene group having 6 to 18 carbon atoms or a heteroarylene group having 6 to 18 carbon atoms. R may be an aryl group having 6 to 18 carbon atoms, a heteroaryl group having 6 to 18 carbon atoms, or an alkyl group having 1 to 12 carbon atoms. In an implementation, R may be the aryl group having 6 to 18 carbon atoms or the heteroaryl group having 6 to 18 carbon atoms, e.g., R may be the aryl group having 6 to 18 carbon atoms. In Chemical Formula (1), a to c may be natural numbers satisfying a<3, b<3, and c<3, and a, b, and c may not equal zero.

The compound according to an embodiment may include the amine derivative including the 5,10-diaryl-5,10-dihydrophenazine group, and may include a 5,10-diaryl-5,10-dihydrophenazine skeleton. In the compound according to an embodiment, dimethylfluorene, dibenzofuran, dibenzothiophene, phenothiazine, phenoxazine, or the like, substituted at an amine group, may be substituents having plenty of electrons. Thus, hole transporting efficiency may be improved. According to an embodiment, hole transporting properties may be further improved by introducing a phenothiazine group having plenty of electrons in an aryl amine group showing good hole transporting properties. In addition, in the compound according to an embodiment, the planarity of a molecule may be broken by introducing an aryl group or a heteroaryl group, e.g., a phenylene group, between an amine and phenazine. Thus, a glass transition temperature may be increased. When the compound is used as the hole transporting material, crystallization during driving of the organic EL device may not easily occur, and durability of the hole transport layer may be improved. In an implementation, a substituent of the phenazine may be an aryl group, a heteroaryl group, or an alkyl group. Thus, electron distribution of HOMO may be changed, and the transporting properties of the holes may be considered to be improved. The compound according to an embodiment may be used as the hole transporting material. Accordingly, the emission efficiency of the organic EL device in a blue light emitting region and a green light emitting region may be increased, and the lifetime may be increased.

According to an embodiment, the compound may have a low ionization potential and may be liable to be oxidized. Thus, the compound according to an embodiment may be appropriately used as the material of the hole transport layer, and/or as a material for a hole injection layer optionally disposed between the anode and the hole transport layer in the organic EL device.

Examples of the compound according to an embodiment may be represented by the following Compounds 1 to 13.

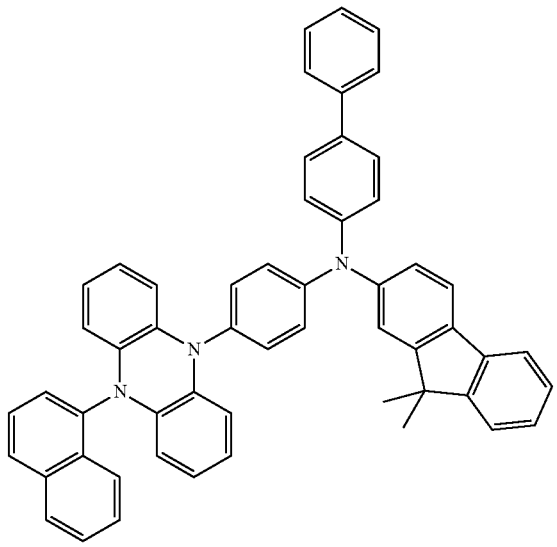

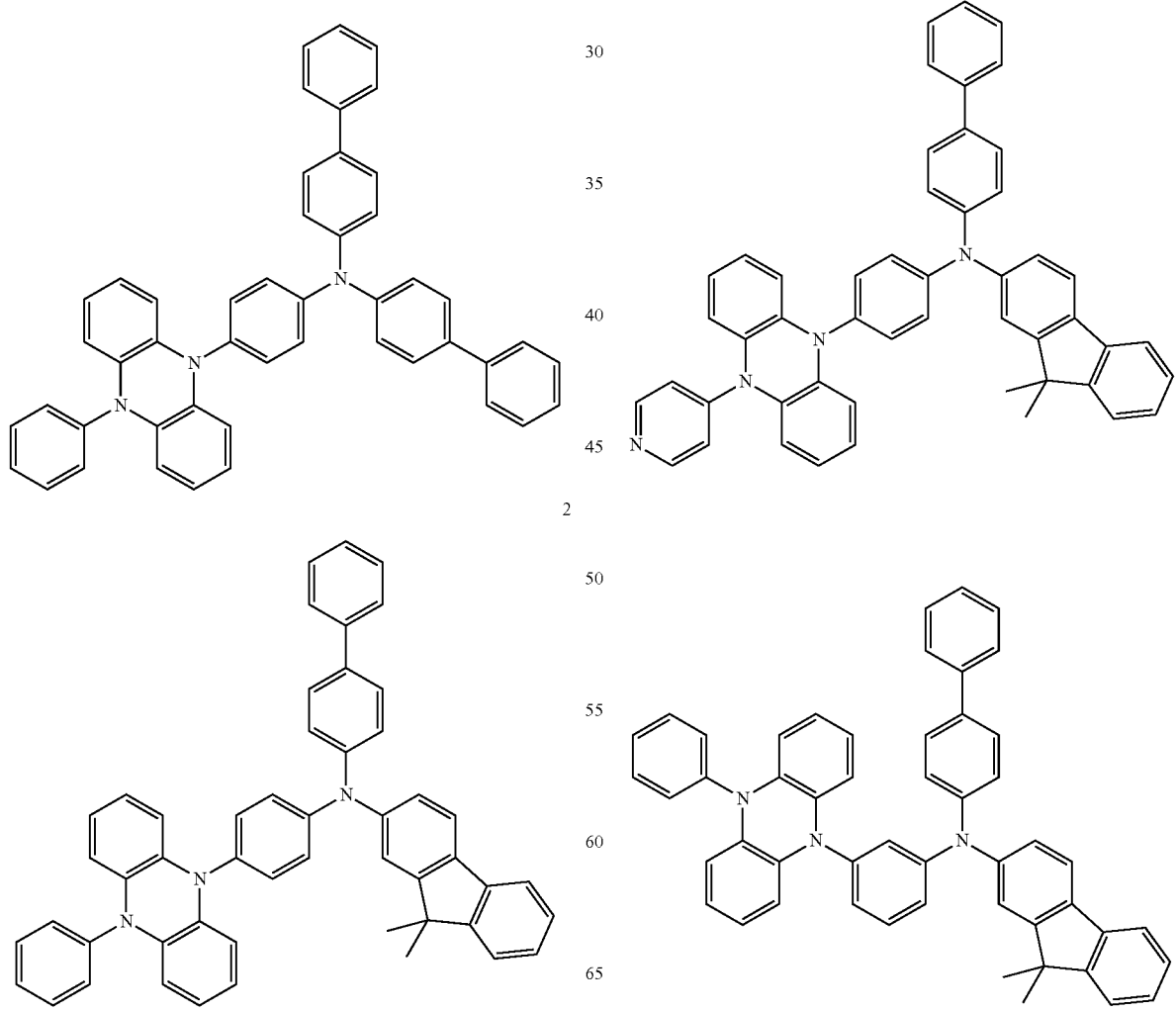

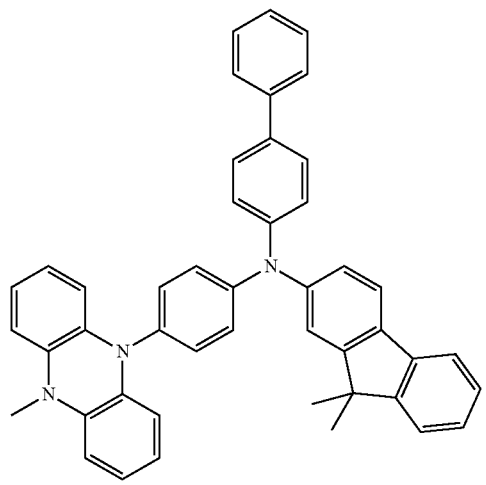
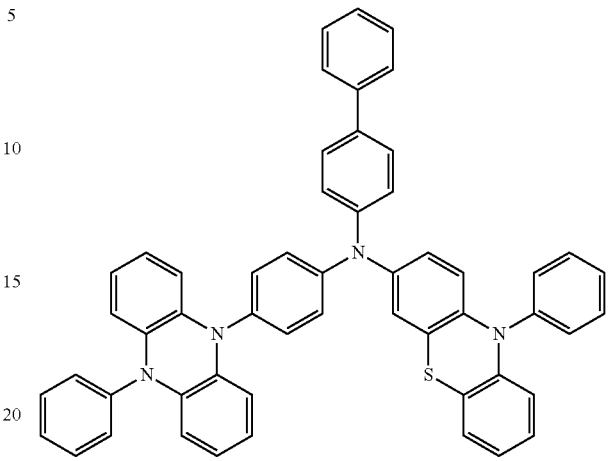
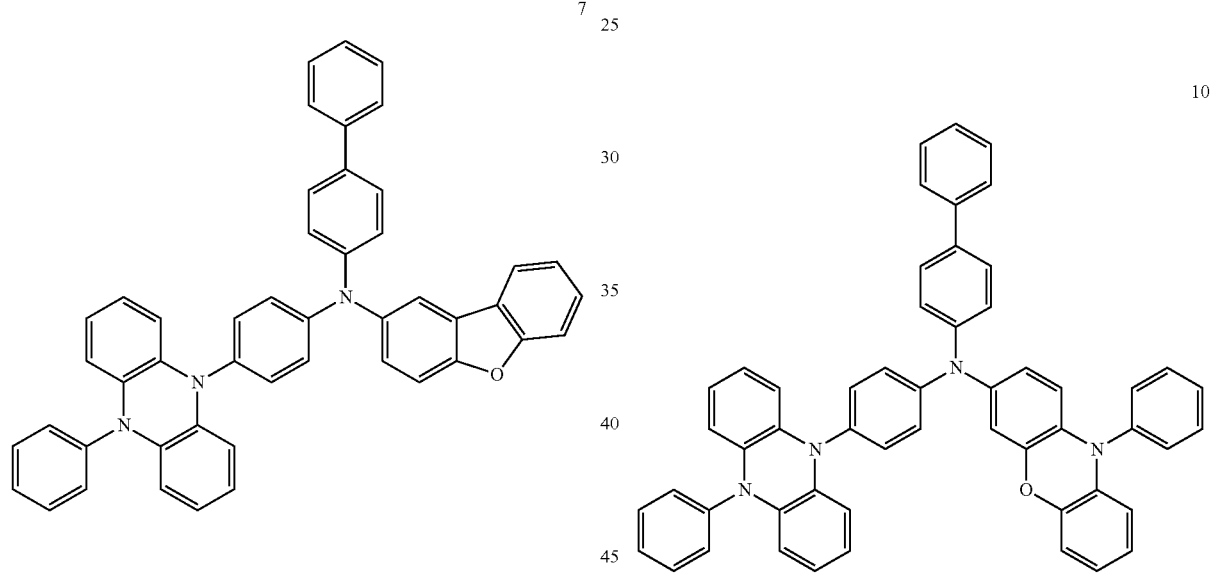
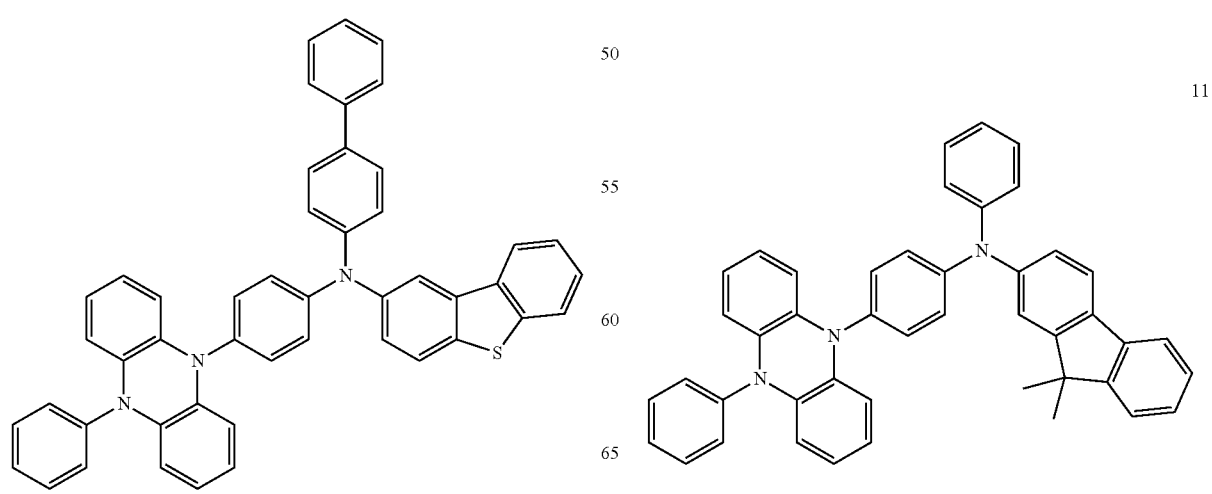

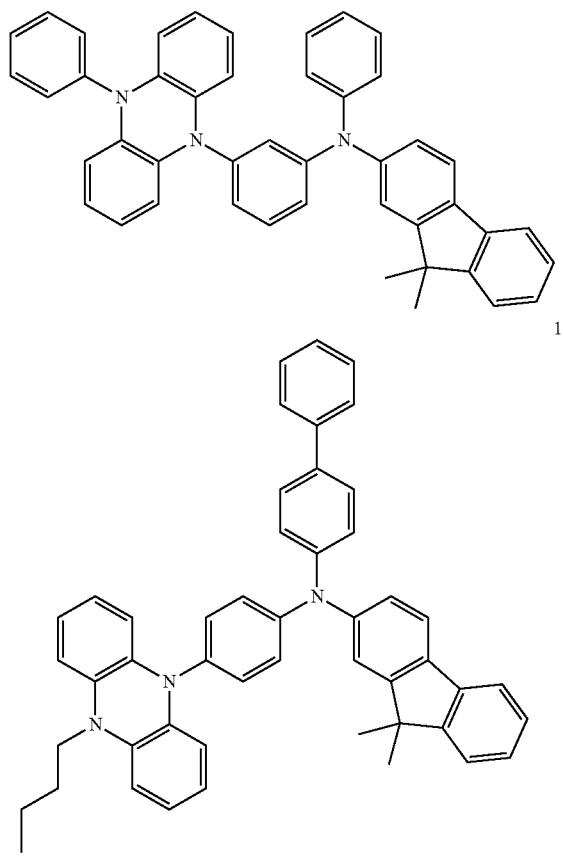

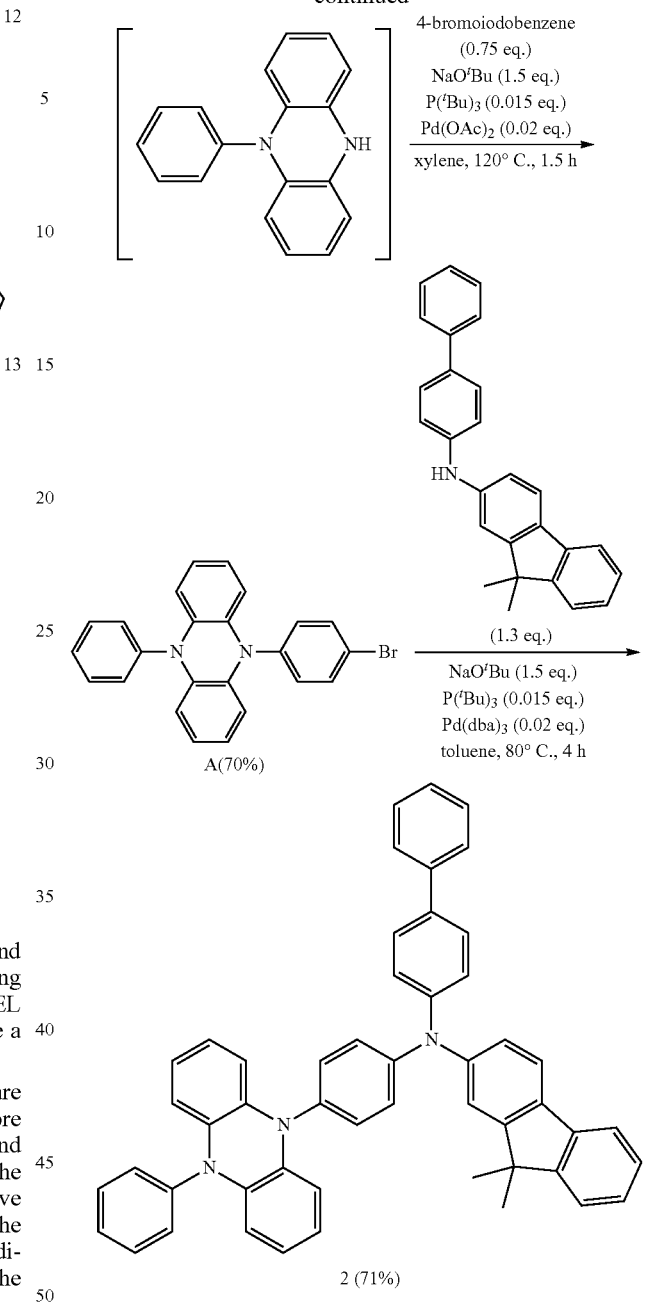

In an implementation, Compound 2, Compound 4, and Compound 10, above, may be used as the hole transporting material or the hole injecting material of an organic EL device. In an implementation, a tertiary amine may make a bond at a para position of an aryl of the compound.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples For example, a synthetic method of the compound according to an embodiment will be explained in the following Reaction Scheme 8 for forming Compound 2.

[Reaction Scheme 8]

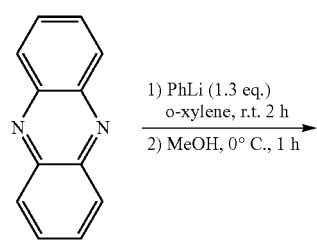

First, 2.01 g of phenazine and 15.4 ml (1.07 M, 1.3 eq) of phenyl lithium were stirred in an o-xylene solvent at room temperature for 2 hours. Then, 5.0 ml of methanol was added and stirred at 0° C. for 1 hour to prepare 10-phenyl-5-hydrophenazine. Into 10-phenyl-5-hydrophenazine, 2.42 g (0.75 eq) of 4-bromoiodobenzene, 2.71 g (1.5 eq) of sodium-tert-butoxide, 0.03 g (0.015 eq) of tri-tert-butylphosphine, and 0.05 g (0.02 eq) of palladium acetate were added, and stirred in a xylene solvent at 120° C. for 1.5 hours to obtain Compound A with the yield of 75%. Into 1.50 g of Compound A, 1.13 g (1.3 eq) of 9,9-dimethyl-N-(4-phenylphenyl)fluorene-2-amine, 0.52 g (1.5 eq) of sodium-tert-butoxide, 0.01 g (0.015 eq) of tri-tert-butylphosphine, and 0.08 g (0.02 eq) of bis(dibenzylideneacetone)palladium were added and stirred in a toluene solvent at 80° C. for 4 hours to obtain Compound 2 with the yield of 71%.

EXAMPLE

Emission efficiency of an organic EL device manufactured by using the compound according to an embodiment as the material of a hole transport layer was measured. The material of the hole transport layer of the organic EL device was above-mentioned Compound 1, which is also illustrated below. In addition, as Comparative Examples, Comparative Compound 1 and Comparative Compound 2, below, were used as the material of the hole transport layer of the organic EL device.

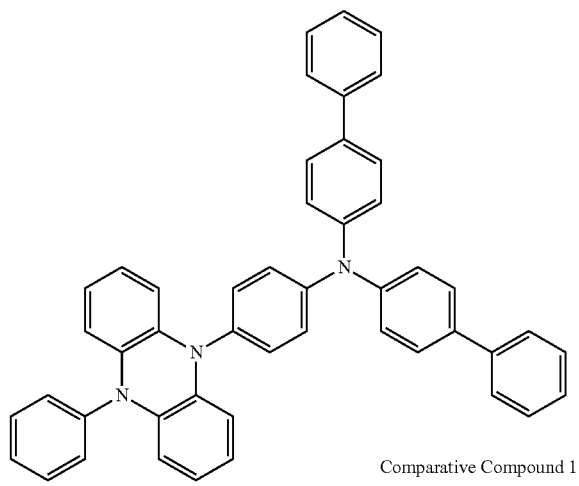

Comparative Compound 1

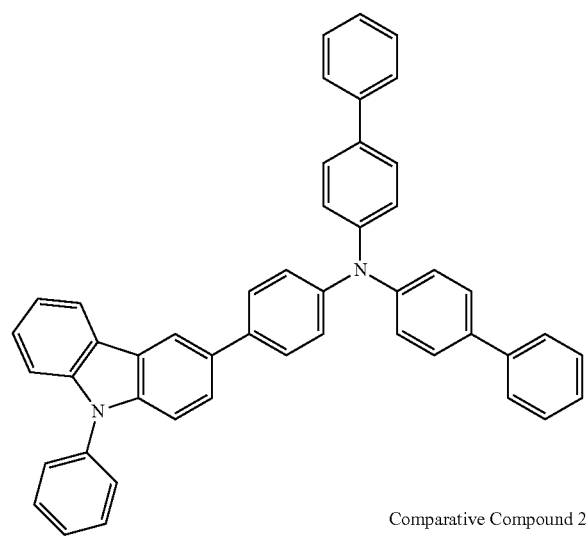

Comparative Compound 2

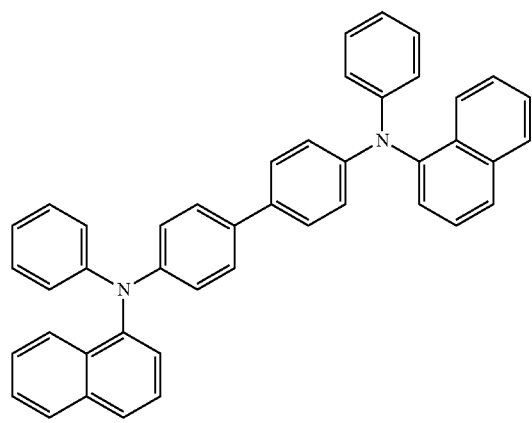

The constitution of an organic EL device used for the measurement is illustrated in FIG. 1. Referring to FIG. 1 the organic EL device 100 included a glass substrate 102, an anode 104 on the glass substrate 102 and formed by using indium tin oxide (ITO), a hole injection layer 106 on the anode 104 and including 4,4',4''-tris(N-(1-naphthyl)-N-phenylamino)triphenylamine (1-TNATA), a hole transport layer 108 on the hole injection layer 106 and including one of Compound 1, Comparative Compound 1, or Comparative Compound 2, an emission layer 110 on the hole transport layer 108 and formed by using a host material including 9,10-di(2-naphthyl)anthracene (AND) doped with tetra-t-butylperylene (TBP) at 3% concentration, an electron transport layer 112 on the emission layer 110 and including Alq3, an electron injection layer 114 on the electron transport layer 112 and including LiF, and a cathode 116 on the electron injection layer 114 and including Al. The thickness of the anode 104 was 150 nm, the thickness of the hole injection layer 106 was 60 nm, the thickness of the hole transport layer 108 was 30 nm, the thickness of the emission layer was 25 nm, the thickness of the electron transport layer 112 was 25 nm, the thickness of the electron injection layer 114 was 1 nm, and the thickness of the cathode 116 was 100 nm.

The emission efficiency of the organic EL device 100 was measured when Compound 1, Comparative Compound 1, or Comparative Compound 2 was used as the material of the hole transport layer 108, by flowing current from a power source through the anode 104 and the cathode 116 to the organic EL device 100. The results are illustrated in the Table 1.

TABLE 1

|  | Compound 1 | Comparative compound 1 | Comparative compound 2 |
| --- | --- | --- | --- |
| Voltage (V) | 7.6 | 7.5 | 8.1 |
| Current efficiency (cd/A) | 6.4 | 6.2 | 5.3 |
| Half life (hr) | 2,200 | 1,500 | 1,200 |

The current efficiency was measured at 10 mA/cm$^2$. The half life was measured at 1,000 cd/m$^2$.

As may be seen in Table 1, the organic EL device manufactured by using Compound 1 as the material of the hole transport layer exhibited improved emission efficiency and increased lifetime, when compared with those of the organic EL devices manufactured by using Comparative compound 1 and Comparative compound 2 as the hole transporting materials.

As described above, by using the compound according to an embodiment as the material of the organic EL material, e.g., as the material of the hole transport layer, the emission efficiency of the organic EL device in a blue light emitting region and a green light emitting region was improved, and the lifetime thereof was increased. Further, the compound according to an embodiment may be used as the material of the hole injection layer of the organic EL device, as well as the hole transport layer, and the same effect may be obtained in both cases. In an implementation, the compound according to an embodiment may be between the anode and the emission layer. In an implementation, the compound according to an embodiment may contact the anode. In an implementation, the compound according to an embodiment may contact the emission layer. In an implementation, the compound according to an embodiment may be used as the material of a passive type organic EL material. In an implementation, the compound according to an embodiment may be used as the organic EL material of an active type organic EL device. In this case, the emission efficiency of the active type organic EL device may be improved and the lifetime thereof may be increased.

An organic EL device including the compound according to an embodiment as the material of a hole transport layer, may be used in an organic EL display apparatus or an illumination system.

By way of summation and review, an organic EL device having high efficiency and a long lifetime may be satisfactorily applied to an organic EL device for a display apparatus. Consideration of normalization, stabilization, durability, or the like of a hole transport layer may increase the efficiency and the lifetime of the organic EL device.

Hole transporting materials applicable in the hole transport layer may include, e.g., anthracene derivatives, aromatic amine compounds, or the like. In addition, 5,10-dihydrophenazine derivatives have been considered as useful materials for increasing the lifetime of the device. 5,10-dihydrophenazine and the derivatives thereof may have a small planar structure in a ligand portion thereof. Thus, crystallization during the driving of an organic EL device may be difficult, and the durability of the hole transport layer may be increased. The 5,10-dihydrophenazine derivatives may be used as the raw materials of the hole transport layer, and may be appropriately used as the raw materials of a hole injection layer or a buffer layer optionally disposed between an anode and a hole transport layer. However, an organic EL device manufactured by using the above-described materials may not have a sufficient emission lifetime. Thus, an organic EL device capable of being driven with higher efficiency by a low voltage and having long lifetime may be desirable. For example, the emission efficiency of the organic EL device may be low in a blue light emitting region, when compared with a red light emitting region and a green light emitting region. Thus, the improvement of the emission efficiency in the blue light emitting region may be desirable.

The embodiments may provide an organic EL material capable of manufacturing an organic EL device having improved emission efficiency and increased lifetime.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:
1. An organic electroluminescence material represented by Chemical Formula 1:

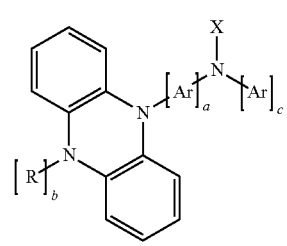

wherein:

X is a monovalent group represented by Chemical Formula (2), Chemical Formula (3), Chemical Formula (4), Chemical Formula (5), Chemical Formula (6), Chemical Formula (7), Chemical Formula (8), Chemical Formula (9), Chemical Formula (10), Chemical Formula (11), Chemical Formula (13), or Chemical Formula (14), each Ar is independently an aryl group having 6 to 18 carbon atoms or a heteroaryl group having 6 to 18 carbon atoms, R is an aryl group having 6 to 18 carbon atoms, a heteroaryl group having 6 to 18 carbon atoms, or an alkyl group having 1 to 12 carbon atoms, and a, b, and c are each independently 1 or 2,

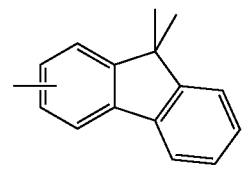

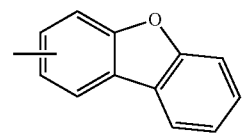

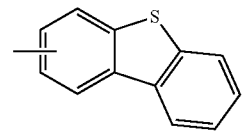

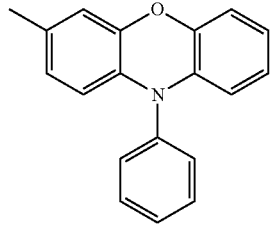

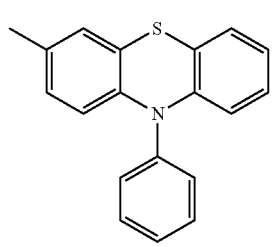

-continued (7)
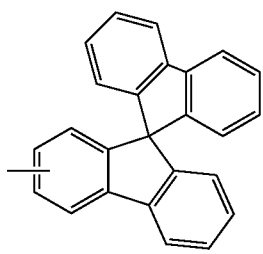

(8)
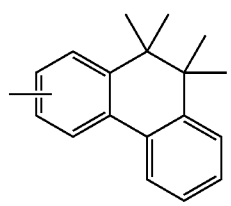

(9)
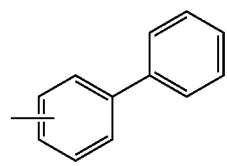

(10)
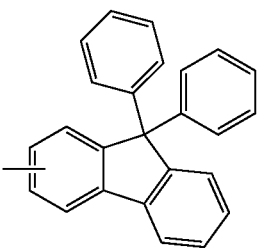

(11)
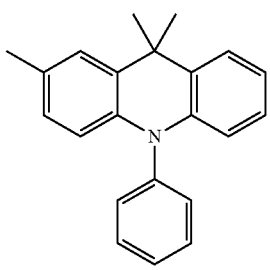

(13)
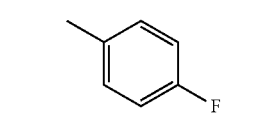

(14)
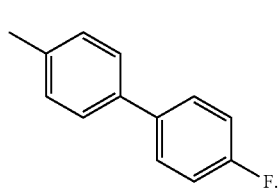

2. The organic electroluminescence material as claimed in claim 1, wherein the organic electroluminescence material represented by Chemical Formula (1) is a hole transporting material.

3. The organic electroluminescence material as claimed in claim 1, wherein the organic electroluminescence material represented by Chemical Formula (1) is a hole injecting material.

4. The organic electroluminescence material as claimed in claim 1, wherein the organic electroluminescence material represented by Chemical Formula (1) is Compound 1, Compound 2, Compound 3, Compound 4, Compound 5, Compound 6, Compound 7, Compound 8, Compound 9, Compound 10, or Compound 13, below:

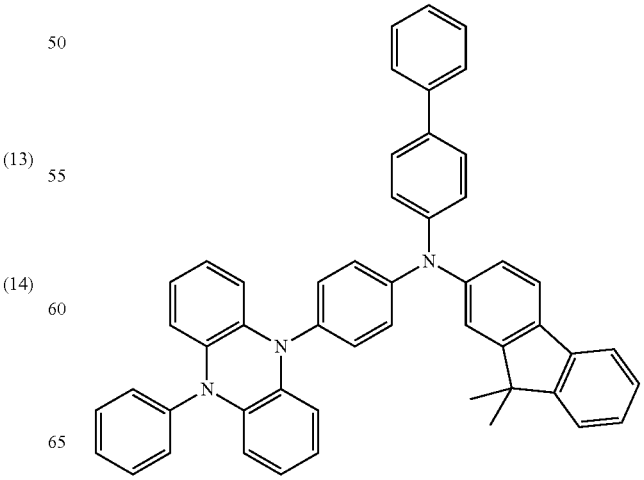

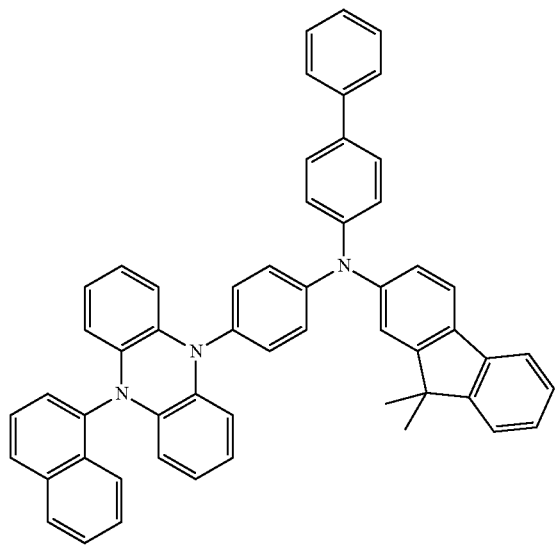
3
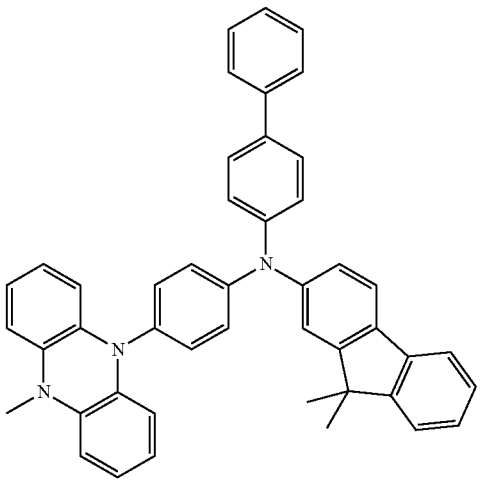
6
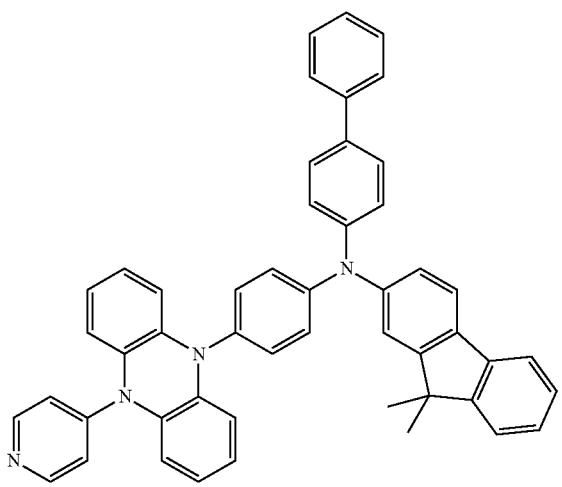
4
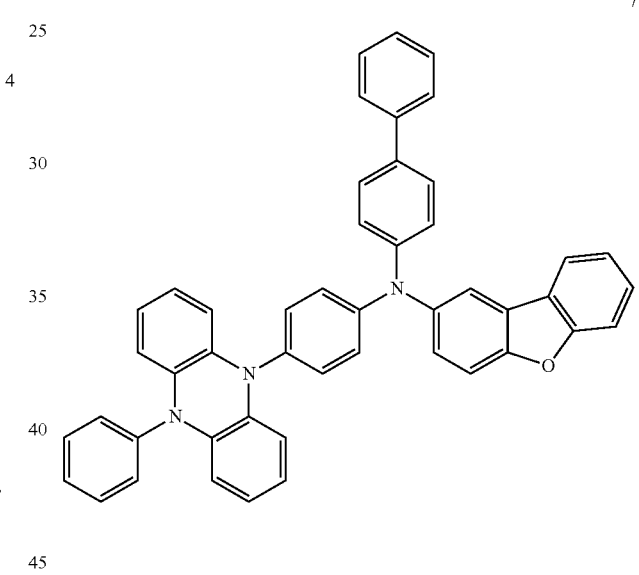
7
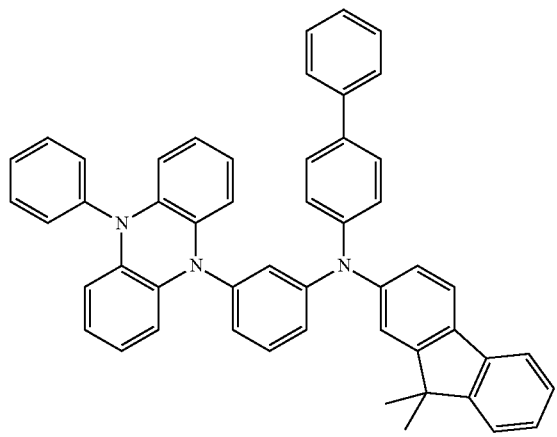
5
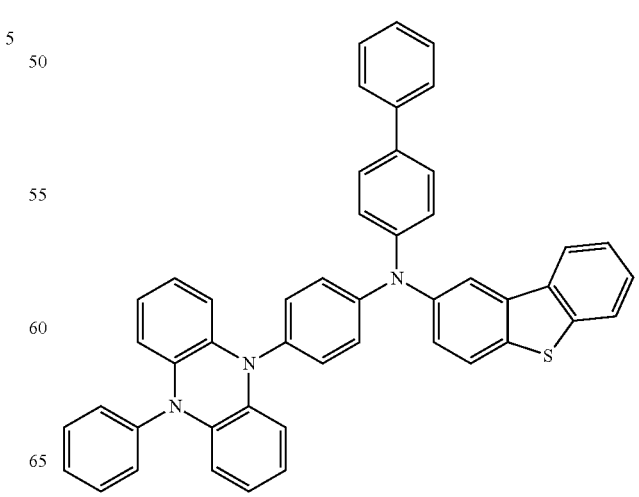
8

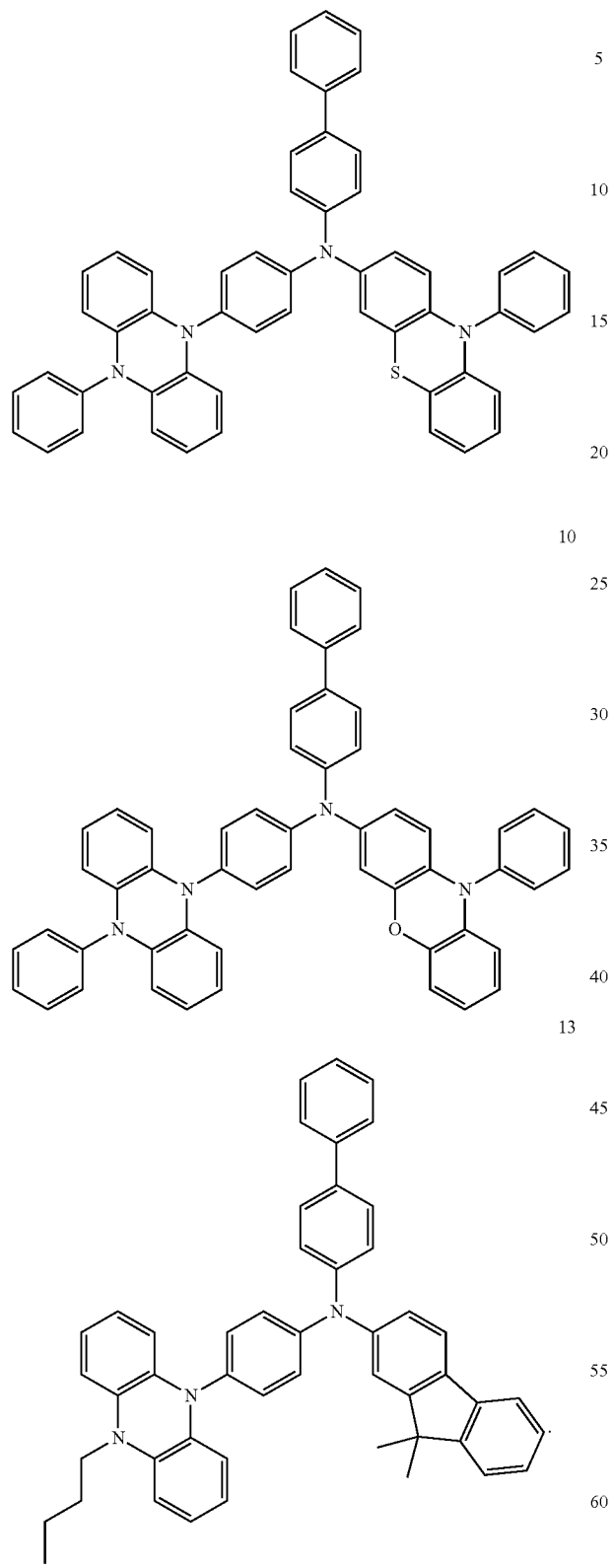

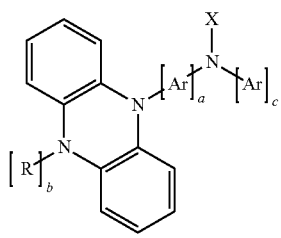

wherein:

X is a monovalent group represented by Chemical Formula (2), Chemical Formula (3), Chemical Formula (4), Chemical Formula (5), Chemical Formula (6), Chemical Formula (7), Chemical Formula (8), Chemical Formula (9), Chemical Formula (10), Chemical Formula (11), Chemical Formula (13), or Chemical Formula (14), each Ar is independently an aryl group having 6 to 18 carbon atoms or a heteroaryl group having 6 to 18 carbon atoms, R is an aryl group having 6 to 18 carbon atoms, a heteroaryl group having 6 to 18 carbon atoms, or an alkyl group having 1 to 12 carbon atoms, and a, b, and c are each independently 1 or 2,

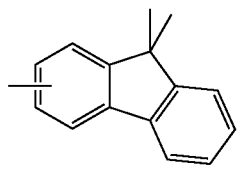

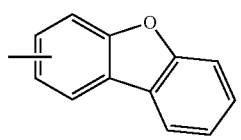

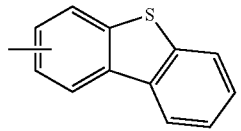

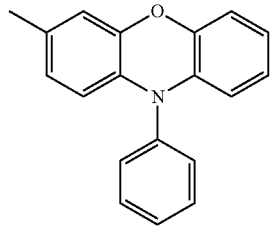

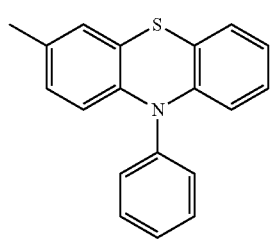

5. An organic electroluminescence device comprising an organic electroluminescence material represented by Chemical Formula (1):

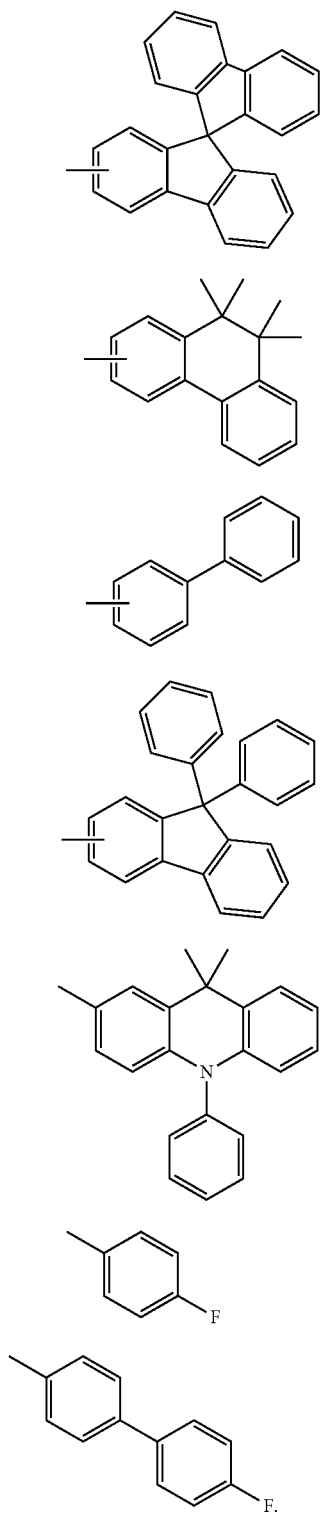

6. The organic electroluminescence device as claimed in claim 5, wherein the organic electroluminescence material is a hole transporting material.

7. The organic electroluminescence device as claimed in claim 5, wherein the organic electroluminescence material is a hole injecting material.

8. The organic electroluminescence device as claimed in claim 5, wherein the organic electroluminescence material represented by Chemical Formula (1) is Compound 1, Compound 2, Compound 3, Compound 4, Compound 5, Compound 6, Compound 7, Compound 8, Compound 9, Compound 10, or Compound 13, below:

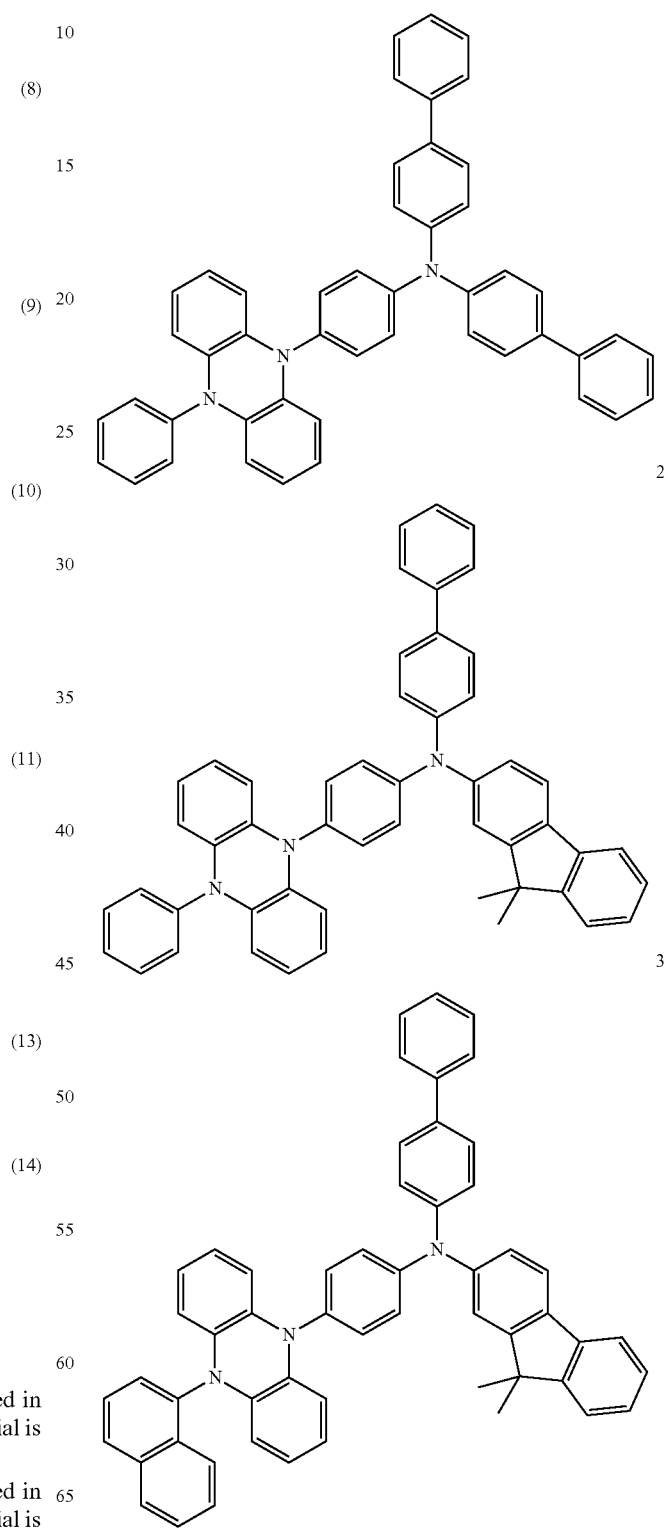

4
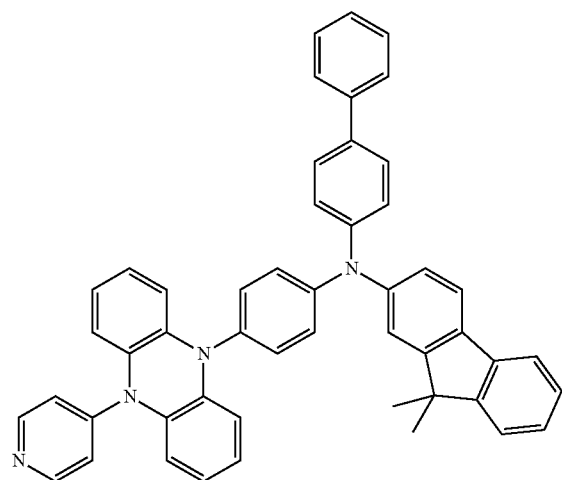
5
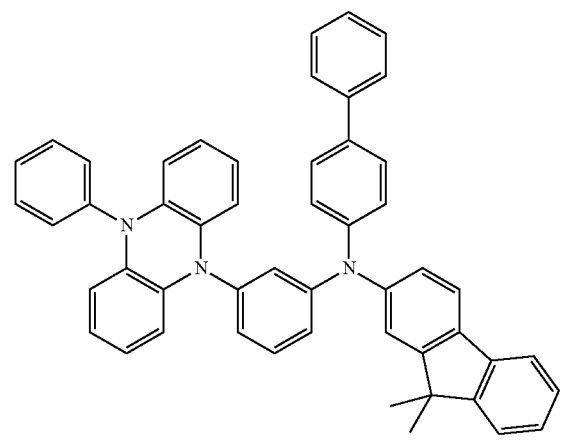
6
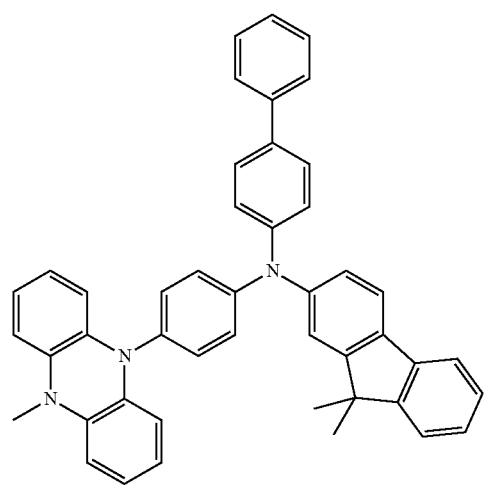
7
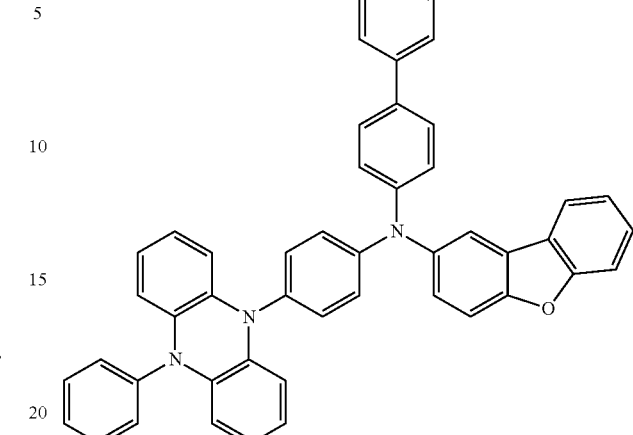
8
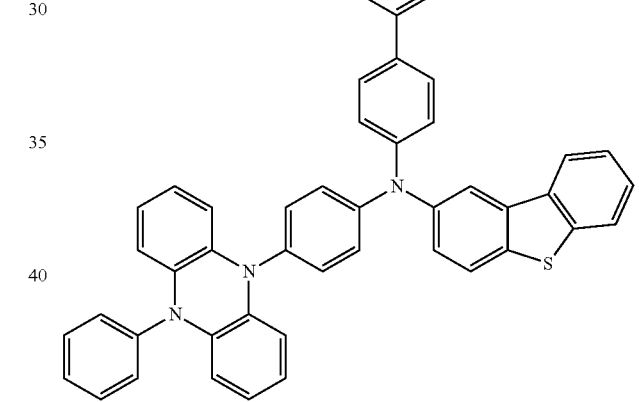
9
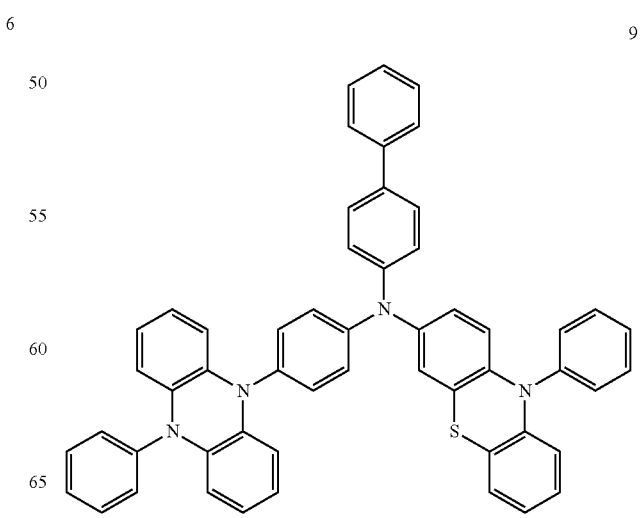

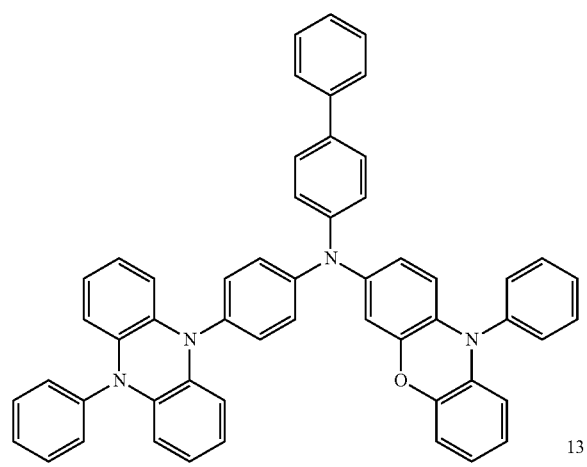
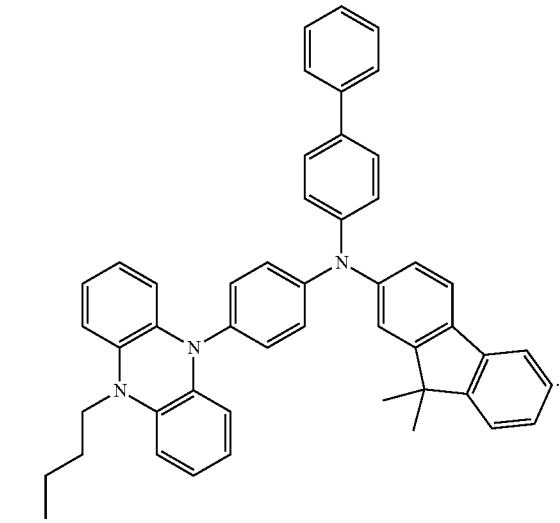
9. An organic electroluminescence device comprising an organic electroluminescence material represented by Compound 1, Compound 2, Compound 3, Compound 4, Compound 5, Compound 6, Compound 7, Compound 8, Compound 9, Compound 10, Compound 11, Compound 12, or Compound 13, below:
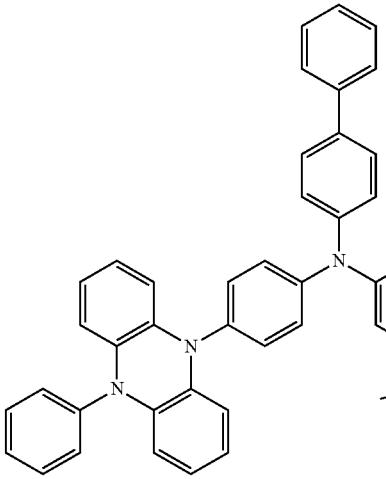
2
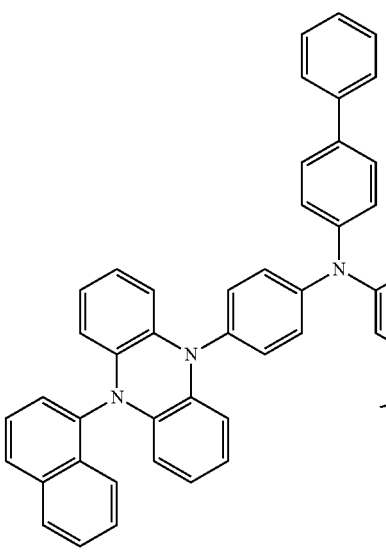
3
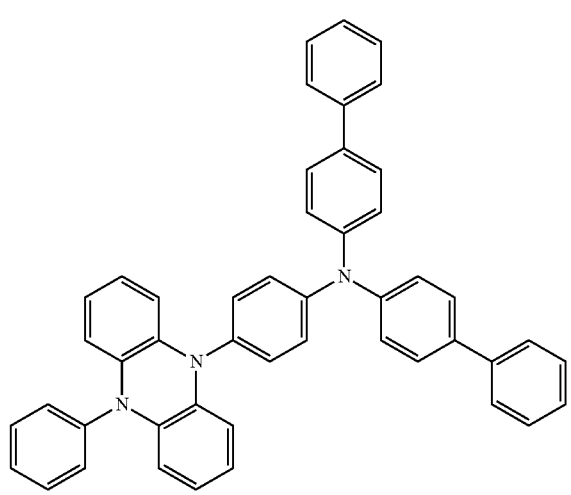
1
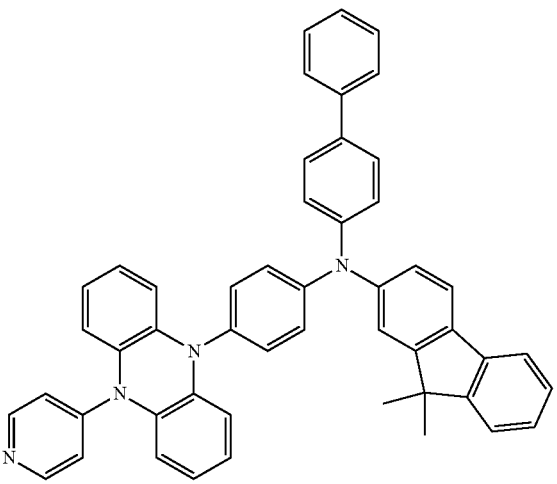
4

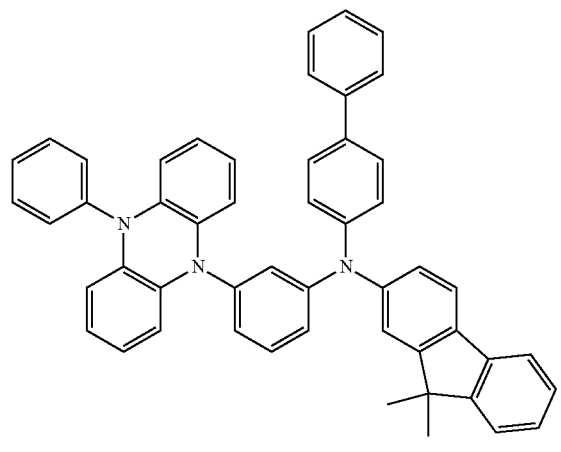
5
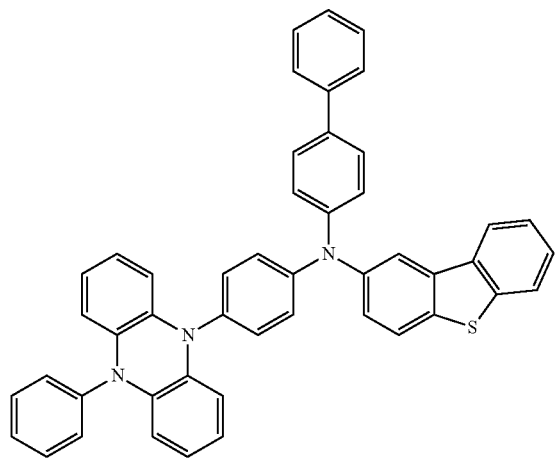
8
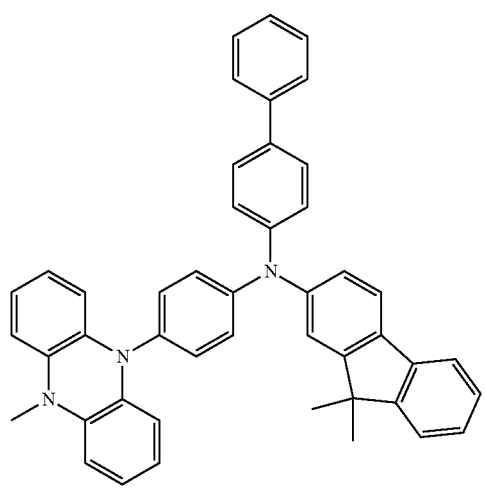
6
9
7
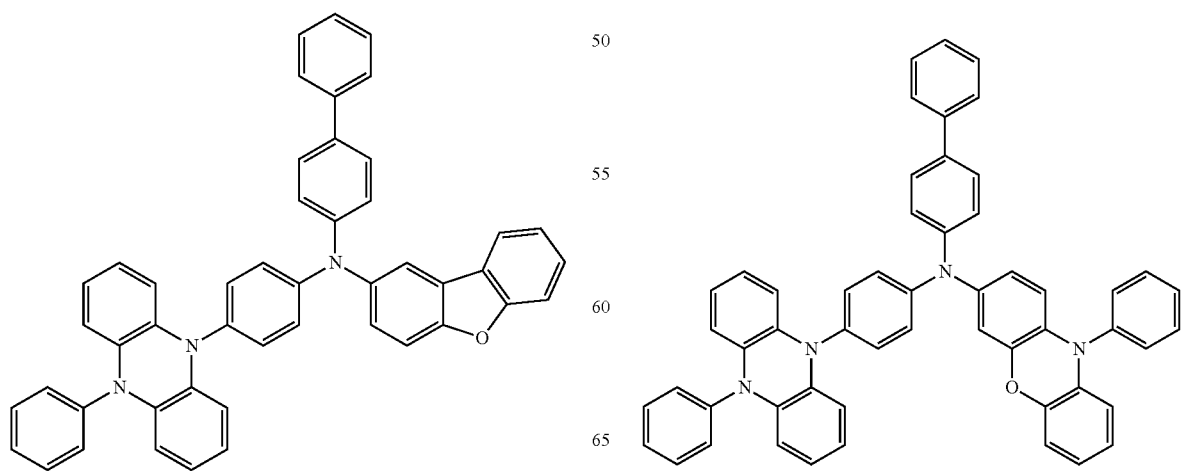
10

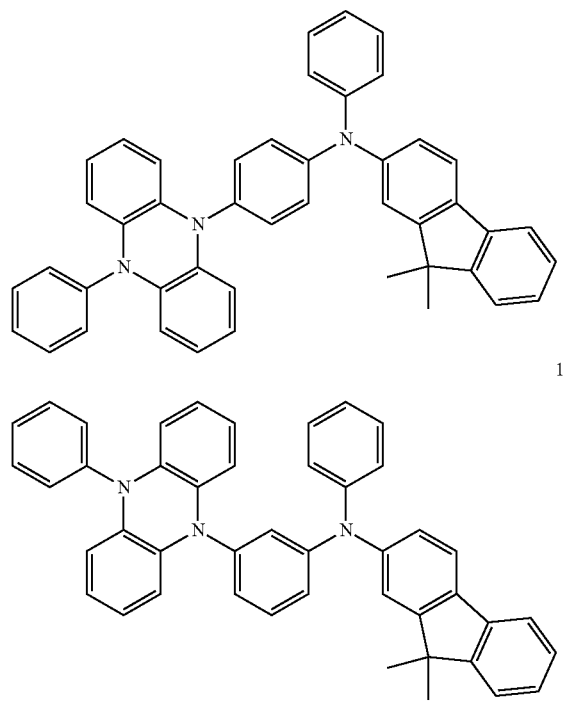
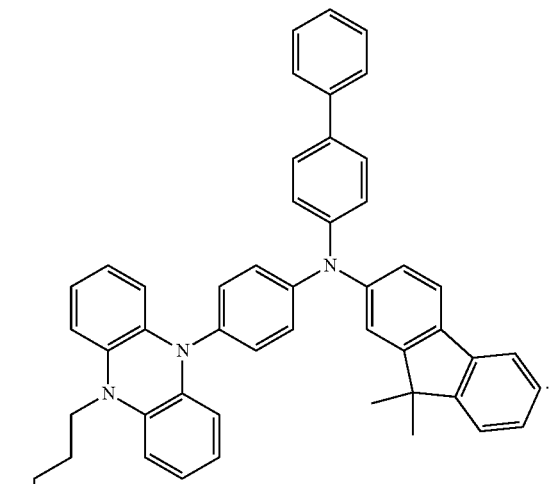
* * * * *